(12) United States Patent
Hardcastle, III

(10) Patent No.: US 6,533,452 B1
(45) Date of Patent: Mar. 18, 2003

(54) ACCELERATED WEATHERING TEST APPARATUS WITH SOAKING CYCLE

(75) Inventor: Henry K. Hardcastle, III, Sunrise, FL (US)

(73) Assignee: Atlas Material Testing Technology, L.L.C., Chicago, IL (US)

( * ) Notice: Subject to any disclaimer, the term of this patent is extended or adjusted under 35 U.S.C. 154(b) by 0 days.

(21) Appl. No.: 10/016,204

(22) Filed: Oct. 30, 2001

(51) Int. Cl.$^7$ .............................................. G01N 17/00

(52) U.S. Cl. .............................. 374/57; 374/5; 73/865.6

(58) Field of Search ........................... 374/57, 4–7, 45, 374/47; 73/865.6, 150 R

(56) References Cited

U.S. PATENT DOCUMENTS

| | | | |
|---|---|---|---|
| 1,870,512 A | * 8/1932 | Jameson | ...................... 374/57 |
| 2,945,417 A | 7/1960 | Caryl et al. | |
| 3,116,977 A | 1/1964 | Grabowski et al. | |
| 3,224,266 A | 12/1965 | Klippert | |
| 3,327,536 A | 6/1967 | Fitzgerald | |
| 3,500,682 A | 3/1970 | Newfield | |
| 3,501,942 A | 3/1970 | Fitzgerald et al. | |
| 3,521,966 A | 7/1970 | Archer | |
| 3,521,967 A | 7/1970 | Archer | |
| 3,576,125 A | 4/1971 | Kockott et al. | |
| 3,664,188 A | 5/1972 | Kockott | |
| 3,889,531 A | 6/1975 | Suga | |
| 4,012,954 A | 3/1977 | Klippert | |
| 4,117,712 A | 10/1978 | Hager, Jr. | |
| 4,222,367 A | 9/1980 | Jubb | |
| 4,282,181 A | * 8/1981 | Pierce | ...................... 73/865.6 |

(List continued on next page.)

FOREIGN PATENT DOCUMENTS

JP           3-96835 A    * 4/1991    ............... 73/865.6

OTHER PUBLICATIONS

ASTM Design.G90–94; Standard Practice for Performing Accelerated outdoor Weathering of Nonmetallic Materials Using Concentrated Natural Sunlight; pps. 1333–1342 (Nov. 1994).

ASTM Designation G26–96; Standard Practice for Operating Light–Exposue Apparatus (Xenon–Arc Type) with and without Water for Exposure of Nonmetallic Materials, pps. 1258–1267 (Apr. 1996).

SAE Standard—Accelerated Exposure of Automotive Exterior Materials Using a Controlled Irradiance Water–Cooled Zenon Arc Apparatus—SAE J1960 JUN89; pps. 11.319–11.325 (Jun. 1989).

ASTM Designation D5722–95; Standard Practice for Performing Accelerated Outdoor Weathering of Factory–Coated Embossed Hardboard Using Concentrated Natural Sunlight and a Soak–Freeze–Thaw Procedure; pps. 570–572 (Jul. 1995).

Henry K. Hardcastle III, "Fractional Factorial Approaches to Emmaqua Experiments", printed Jun. 1, 2000; pps. 1–26.

Henry K. Hardcastle III, "Applying Taguchi Designs to EMMAQUA Weathering Experiments", Jul. 12, 2000; pps. 1–16.

Primary Examiner—Diego Gutierrez
Assistant Examiner—Stanley J. Pruchnic, Jr.
(74) Attorney, Agent, or Firm—Vedder Price Kaufman & Kammholz

(57) ABSTRACT

An accelerated weathering test apparatus for concentrating solar irradiance upon and immersing at least one test specimen including at least one support member and an operative portion operatively connected to the at least one support member. The operative portion includes a mirror bed, at least one standard and a channel. The operative portion is moveable relative to the at least one support member from a first operative position to a second operative position. A target board is disposed in the channel for supporting the at least one test specimen for exposure to concentrated solar radiation when the operative portion is disposed in the first operative position and immersion in a fluid when the operative portion is disposed in the second operative position.

20 Claims, 5 Drawing Sheets

U.S. PATENT DOCUMENTS

| | | |
|---|---|---|
| 4,503,902 A | 3/1985 | Zolik |
| 4,544,995 A | 10/1985 | Suga |
| 4,615,481 A | 10/1986 | Tanaami et al. |
| 4,644,166 A | 2/1987 | Sturm et al. |
| 4,659,290 A | 4/1987 | Kundert |
| 4,698,507 A | 10/1987 | Tator et al. |
| 4,722,669 A | 2/1988 | Kundert |
| 4,760,748 A | 8/1988 | Katayanagi et al. |
| 4,807,247 A  * | 2/1989 | Robbins |
| 4,817,447 A  * | 4/1989 | Kashima et al. ............ 73/865.6 |
| 4,995,273 A  * | 2/1991 | Kisima et al. ............. 73/865.6 |

* cited by examiner

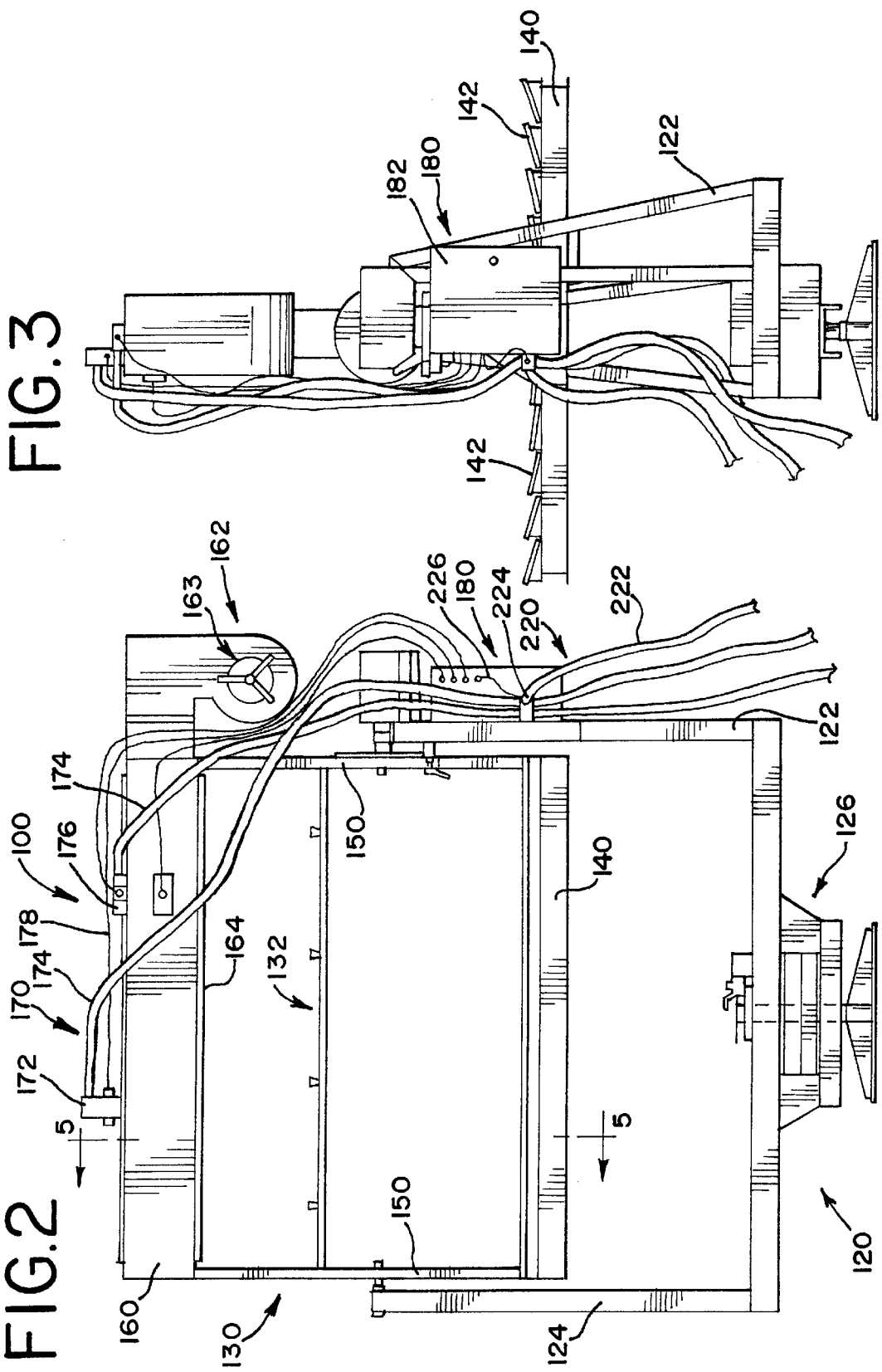

ACCELERATED WEATHERING TEST APPARATUS WITH SOAKING CYCLE

FIELD OF THE INVENTION

The present invention relates generally to a weathering test apparatus of the type used to expose test specimens to solar radiation and other weathering effects on an accelerated basis, and more particularly, to such an improved accelerated weathering test apparatus that provides an automated soaking cycle regardless of the time of day.

BACKGROUND OF THE INVENTION

Manufacturers of exterior coatings, such as paints and finishes, as well as plastics and other components which tend to degrade under exposure to solar radiation and other weathering effects, often want to know how such products will perform following years of exposure. However, such manufacturers typically require such information in a much shorter time than it would take to exposure such materials to weathering effects under normal conditions. Accordingly, accelerated weathering test apparatus have been developed which accelerate the effects of weathering due to outdoor exposure in a much shorter time so that manufacturers need not actually wait five or ten years in order to determine how their products will hold up after five or ten years of actual outdoor exposure.

One conventional outdoor accelerated weathering test apparatus is disclosed in U.S. Pat. No. 4,807,247 issued to Robins, III, and shown in FIG. 1. The aforementioned test device includes a Fresnel-reflecting solar concentrator having a frame 32 with a series of ten flat mirrors 34,36 which focus natural sunlight onto a series of test specimens secured to a target board measuring approximately six (6) inches wide by fifty-five (55) inches long. The Fresnel-reflecting solar concentrator directs solar radiation onto the target board area with an intensity of approximately eight suns. Both the bed 32 which supports the mirrors 34, 36 of the solar concentrator, and the target board, are supported by a frame which can be rotated to follow daily movements of the sun. A solar tracking mechanism responsive to the position of the sun, controls the operation of an electric motor used to rotate the test apparatus to follow movements of the sun.

The axis of rotation of the test machine is oriented in a north-south direction, with the north elevation having altitude adjustment capability to account for variation in the sun's altitude at various times during the year. Such known testing apparatus are also provided with an air tunnel 44 mounted above the target board. An air deflector causes air escaping from the air tunnel to be circulated across the test samples mounted to the target board to prevent the test samples from overheating due to the concentrated solar radiation to which they are exposed. A squirrel cage blower 48 communicates with the air tunnel 44 for blowing cooling ambient air there through. Devices and mechanisms have been adapted to control the blower in order to maintain the temperature of the target test samples substantially constant during daylight hours despite variations in the daytime ambient air temperature, and despite variations in the solar radiation intensity. In addition, water spray nozzles 60 are provided proximate to target board for wetting the test samples at periodic intervals to simulate the weathering effects of humidity, dew, rain, etc.

Standardized testing methods have been developed for operating outdoor accelerated weathering test apparatus of the type described above. The American Society for Testing and Materials (ASTM) has issued standards such as, but not limited to, standard G90, which is directed to testing procedures and operating parameters for conducting such outdoor accelerated weathering tests. Other standards have been developed by the Society of Automotive Engineers (SAE), Ford, International Standards Organization (ISO), American National Standards Institute (ANSI), Japan Industrial Standard (JIS) and other such standards organizations which are directed to accelerated weathering tests. However, no standard has been developed which incorporates a soaking cycle into an outdoor, natural light accelerated weathering test cycle. Standard D5722 was developed for accelerated finish failure involving loss of film integrity, such as cracking, peeling and flaking of factory-coated embossed hardboard. This Standard accelerates long-term weathering effects by subjecting the test specimens to concentrated natural sunlight (with optional periodic daytime surface water spray) plus a remote soak-freeze-thaw cycle. The Standard procedure requires removing the target board with attached test specimens from the testing apparatus and immersing the target board in a deionized water soak tank maintained at 21° C.+/−3° C. (70° F.+/−5° F.) for one hour. After soaking, the target board with attached test specimens is placed in a freezer maintained at −18° C.+/−3° C. (0° F.+/−5° F.) for 12 hours. The following morning, the test specimens are allowed to thaw for a minimum of one hour under laboratory ambient conditions. The target board with attached test specimens is then remounted on the exposure device in accordance with prior practice.

It has been recognized by independent study that a soaking cycle is a significant and important variable for evaluating degradation of materials in accelerated weathering tests. The inventor hereof has conducted numerous experiments in the field of accelerated weathering testing which verify and confirm that a soaking period is a significant and important variable in such testing. The results of these experiments were discussed in technical papers prepared, published and presented by the inventor titled "Fractional Factorial Approaches to Emmaqua Experiments" and "Applying Taguchi Designs to Emmaqua Weathering Experiments."Both papers document the results of the background research related to different techniques for accelerated weathering tests which concludes that immersion plays a critical role in weathering degradations.

Apart from outdoor accelerated weathering test devices of the type described above, other test devices are also known which utilize an artificial source of radiation and immersion in water to exposure test samples. An example of such a test devices are disclosed in U.S. Pat. No. 3,116,977, issued to Grabowski, et al.; U.S. Pat. No. 3,224,266, issued to Klippert; U.S. Pat. No. 3,266,306, issued to Arnold, et al.; U.S. Pat. No. 3,685,969, issued to Young III; U.S. Pat. No. 3,936,273, issued to Powell; U.S. Pat. No. 4,012,954, issued to Klippert; U.S. Pat. No. 4,282,181, issued to Pierce; U.S. Pat. No. 4,698,507, issued to Tator, et al.; and other conventional testing methods.

U.S. Pat. No. 3,116,977 discloses an apparatus to screen corrosion inhibitors by immersing metallic test specimens into a heated bath of water having the inhibitor dissolved therein, withdrawing the metallic specimens and heating them and continuing the periodic immersion and withdrawal for a substantial period. There is no provision for exposure to solar radiation or other light source.

U.S. Pat. No. 3,224,266 claims an apparatus for testing samples under conditions such as humidity, rain, or complete immersion in liquid, heat and air circulation as well as light and dark periods with controlled changeover between light and dark. It provides for heating with a heater source of warm air in addition to heat from the illumination source. This prior apparatus does not provide for exposure to solar radiation or rapid sequencing of immersion followed by exposure to solar radiation.

U.S. Pat. No. 3,266,306 describes an apparatus to test resistance of materials to humidity by exposing them to steam pressure in a chamber. No solar radiance exposure or other light source exposure is practiced in this prior art patent.

U.S. Pat. No. 3,685,969 discloses an apparatus for testing the strength of specimens under corrosive conditions. Specimens under stress are subjected to intermittent immersion using gravity flow of a corrosive fluid to and from a fixed tank with the specimens. Solar radiation or other light source exposure is not mentioned.

U.S. Pat. No. 3,936,273 discloses an apparatus for determining the corrosion protection performance of a fluid. This apparatus rotates test specimens mounted on a shaft through the liquid and thereafter may maintain this test specimens for extended periods in the fluid prior to examination for the degree of corrosion. This prior art patent does not provide for solar radiation or other light source exposure.

U.S. Pat. No. 4,012,954 claims an apparatus for testing light-and weather-resisting properties of materials by employing a mirror reflecting infrared and passing ultraviolet and visible light from an illumination source together with a second mirror reflecting visible and ultraviolet light while transmitting the infrared portion. Samples on a horizontal support can be flooded with water, drained or water cooled, and may also be air cooled. In this prior art patent, there is no exposure to solar radiation.

U.S. Pat. No. 4,282,181 describes an apparatus for accelerating corrosion testing of parts in which the parts are lowered into a corrosive medium and then raised into a drying zone for predetermined, repetitive periods. No mention of solar radiance or other light source exposure is made.

U.S. Pat. No. 4,698,507 describes an apparatus for testing for resistance of immersion swelling, drying shrinkage, thermal expansion and thermal contraction under light exposure. The test samples are placed on a mount on a rotating shaft which immerses the sample in water, heats and dries it, and exposes it to light before cooling it by again immersing it in water. The corrosion resistant chamber enclosing the rotating shaft is composed of a lower tank base and a cover fitted with fluorescent lights and infrared heating strip, a thermocouple and a viewing port. The test liquid is maintained at a constant temperature by fluid flow through a heat exchanger using a thermocouple and a controller. In this prior art patent, there is no exposure to solar radiation.

While such test devices have the advantage of permitting precise control over radiation intensity, temperature, and humidity, such test devices fail to duplicate the actual light spectrum of natural sunlight to which the samples under test will actually be exposed in everyday use. It has been acknowledged and recognized that the outdoor (natural) light source and indoor (artificial) light source test apparatus are distinct from one another and provide different sets of empirical data. For example, ASTM has issued Standard G26 and SAE has issued Standard Test Method J1960 for operating an artificial light-exposure apparatus (Xenon-Arc type) with and without water for exposure of nonmetallic materials.

Outdoor accelerated weathering test devices of the type described above in regard to U.S. Pat. No. 4,807,247 (FIG. 1), have the advantage of using natural sunlight and hence the samples under test are exposed to the actual spectrum of sunlight. However, one disadvantage of outdoor accelerated weathering test devices has been discovered, namely the inability to include automated soaking cycles into a test method.

Conventional testing methods which include a soaking cycle are disadvantageous in that they are very time and labor intensive. Accordingly, a very limited number of exposure and immersion cycles can be completed with the requisite degree of reliability within a certain period. The procedure for the conventional testing method includes exposing the test specimens to concentrated sunlight as per ASTM G90 or other acceptable standard operating procedure. Generally, the steps of the soaking test cycle procedure include: (1) mounting specimens in frames; (2) rotating the apparatus to an inverted position to provide access to the target board area; (3) centering the frames with specimens on the target board; (4) attaching the frames to the target board using screws or other appropriate attachment mechanisms; (5) activating the apparatus cooling air blower; (6) activating the apparatus solar tracking system; (7) rotating and focusing the apparatus to provide solar irradiance on the specimens; (8) tracking the sun throughout the daytime; (9) deactivating the blower and tracking system in the evening; (10) rotating the apparatus to the inverted position to provide access to the target board area; (11) removing the attachment mechanisms from the frames; (12) removing the frames and specimens from the apparatus; (13) transporting the frames into the laboratory where the soak tanks are located; (14) filling a tank with de-ionized water; (15) submerging a heating element in the tank; (16) activating the heater element to warm the water; (17) inserting a temperature probe into the water which is connected to a heater controller for controlling the heater element and water temperature; (18) setting the water temperature controller to a predetermined set point; (19) immersing the specimens in the water contained in the soak tank; (20) immersing the specimens in the soak tank for predetermined period of time (usually overnight); (21) removing the specimens from the soak tank after soaking for a predetermined amount of time; (22) transporting the specimens from the soak tank in the laboratory outside to the apparatus; and (23) reattaching the specimens in the frames to the apparatus target board using screws or other appropriate attachment mechanisms. This cycle of irradiance-specimen removal-specimen immersion-specimen remounting-irradiance is continued for a predetermined number of cycles.

There are several disadvantages of this conventional soaking cycle test method. One disadvantage is that a technician must dismount the frame and test specimens from the target board prior to the immersion step. This would be required hundreds of times throughout a single exposure test (hundreds of cycles). The dismount-remount steps are labor-intensive, expensive and inefficient. Further, the technician is required to remount the frames and test specimens onto the target boards after the immersion step. Again, this may be required hundreds of times for a single exposure test which is labor intensive, expensive and inefficient. Another disadvantage is that manual removal and remounting requires lengthy periods of time. Further, manual dismount and remount is subject to mistakes such as improper positioning of test specimens with respect to cooling air, irradiance or correct machine, all of which introduce sizable errors into the test cycle and skew the results of such an expensive test. Another disadvantage is that the amount of time required to dismount and remount specimens makes multiple immersion cycles within a 24-hour period highly unattractive for experimentation or testing. In the prior art, during periods of solar irradiance (daytime) only water spray was used to provide moisture to the test specimen surface while the test specimens were mounted on the target board. Yet another disadvantage is that the conventional soaking cycle method requires transportation of specimens from the apparatus target board to remotely located soak tanks (currently inside laboratories). Thus, increasing the probability of damage to specimens due to handling and consequently introducing errors and skewing the accuracy of the test results.

Prior outdoor accelerated weathering test apparatus only provide for spraying of water on the test specimens during periods of solar irradiance. However, soaking periods have been determined to be important and significant with regard to degradation of materials. Incorporating a soaking period in the conventional irradiance cycle test method is labor intensive, expensive, and inefficient. The conventional soaking cycle test method introduces numerous errors into the experimentation process which skew the results of the exposure test preventing reliable interpretation of the test results. Consequently, there exists a need for an improved accelerated weathering test apparatus and method incorporating a soaking cycle.

BRIEF DESCRIPTION OF THE DRAWINGS

FIG. 2 is a side elevation view of one example of an accelerated weathering test apparatus in a first operative position in accordance with one embodiment of the invention.

FIG. 3 is an end elevation view of the accelerated weathering test apparatus of FIG. 2.

DETAILED DESCRIPTION OF A PREFERRED EMBODIMENT OF THE INVENTION

Figure 1:
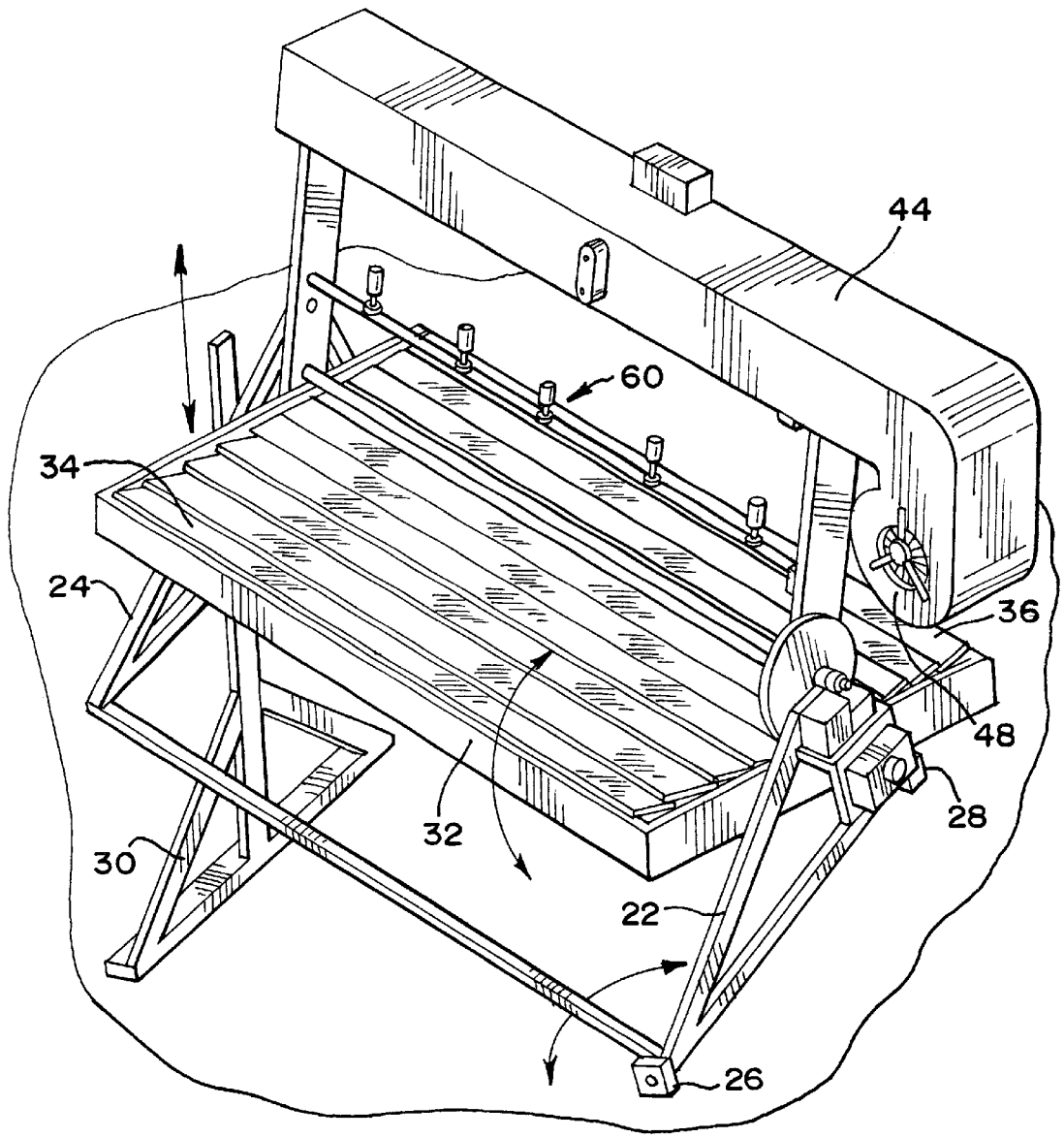
FIG. 1 is a perspective view of a prior art accelerated weathering test apparatus.

Briefly, in one embodiment, the accelerated weathering test apparatus for concentration of solar irradiance upon and immersing at least one test specimen includes at least one support member and an operative portion operatively connected to the at least one support member. The operative portion includes a mirror bed, at least one standard, and a channel. The operative portion is moveable relative to the at least one support member from a first operative position to a second operative position. A target board is disposed in the channel for supporting the at least one test specimen for exposure to concentrated solar irradiance when the operative portion is disposed in the first operative position and immersion in a fluid when the operative portion is disposed in the second operative position.

In one embodiment, the accelerated weathering test apparatus for concentrating solar irradiance upon and immersing at least one specimen includes at least one support member and an operative portion operative connected to the at least one support member including a mirror bed, at least one standard, a channel, and an air circulation mechanism in communication with the channel where the operative portion is moveable relative to the at least one support member from a first operative position to a second operative position includes a target board, a supply system and a control device. The target board is disposed in the channel for mounting the at least one test specimen for exposure to concentrated solar irradiance when the operative portion is disposed in the first operative position and immersion in a fluid when the operative portion is disposed in the second operative position. The supply system includes a first valve and at least one fluid passageway operatively connected to the channel for supplying the fluid to the channel. The control device controls the first valve to supply the fluid to the channel such that the at least one specimen is immersed in the fluid when the operative portion is in the second operative position.

It will be recognized that it is within the teachings of this invention that the control device may be configured in any suitable form. For example, the control device may be configured as an electronic and electrical system of components, mechanical elements, such as handles, timers and levers, for manipulation by an operator or any other suitable configuration. Accordingly, it will be further recognized that the values and each step of the testing cycle may be controlled by an electronic and electrical system or by manual manipulation by an operator of mechanical elements.

In one embodiment, a method for accelerated weathering testing includes providing an accelerated weathering test apparatus including at least one support member and an operative portion operatively connected to the at least one support member including a mirror bed, at least one standard, a channel having a target board disposed therein, an air circulation mechanism in communication with the channel, a supply system including a first valve operatively connected to the channel for supplying a fluid to the channel and a control device for controlling the first valve. The next step includes mounting at least one test specimen on the target board. The next step includes programming the control mechanism to function to execute a test cycle including the steps of: (1) activating the air circulation mechanism; (2) activating a solar tracking system for a first predetermined period of time; (3) deactivating the solar tracking system upon expiration of the first predetermined period of time; (4) rotating the operative portion from the first operative position to the second operative position; (5) deactivating the air circulation mechanism; (6) activating a first valve for a second predetermined period of time from a first operative position normally closed to a second operative position open such that the fluid is supplied through the fluid passageways and the first valve and into the channel; (7) deactivating the first valve from the first operative position to the second operative position upon expiration of the second predetermined period of time such that the fluid in the channel is at a desired level; (8) exposing the at least one test specimen for a third predetermined period of time; removing the fluid from the channel; and (9) repeating the above steps for a desired number of testing cycles.

FIG. 2 shows a side elevation view of an accelerated weathering test apparatus in accordance with an embodiment of the present invention designated generally by reference numeral 100. The accelerated weathering test apparatus 100 concentrates solar irradiance upon and immerses at least one test specimen during a test cycle and includes at least one support member 120 and an operative portion 130 operatively connected to the at least one support member 120. The operative portion 130 includes a mirror bed 140, at least one standard 150 and a channel 160. The operative portion 130 is movable relative to the at least one support member 120 from a first operative position, as shown in FIGS. 2, 3 and 5, to a second operative position, as shown in FIGS. 4 and 6A–C.

Figure 4:
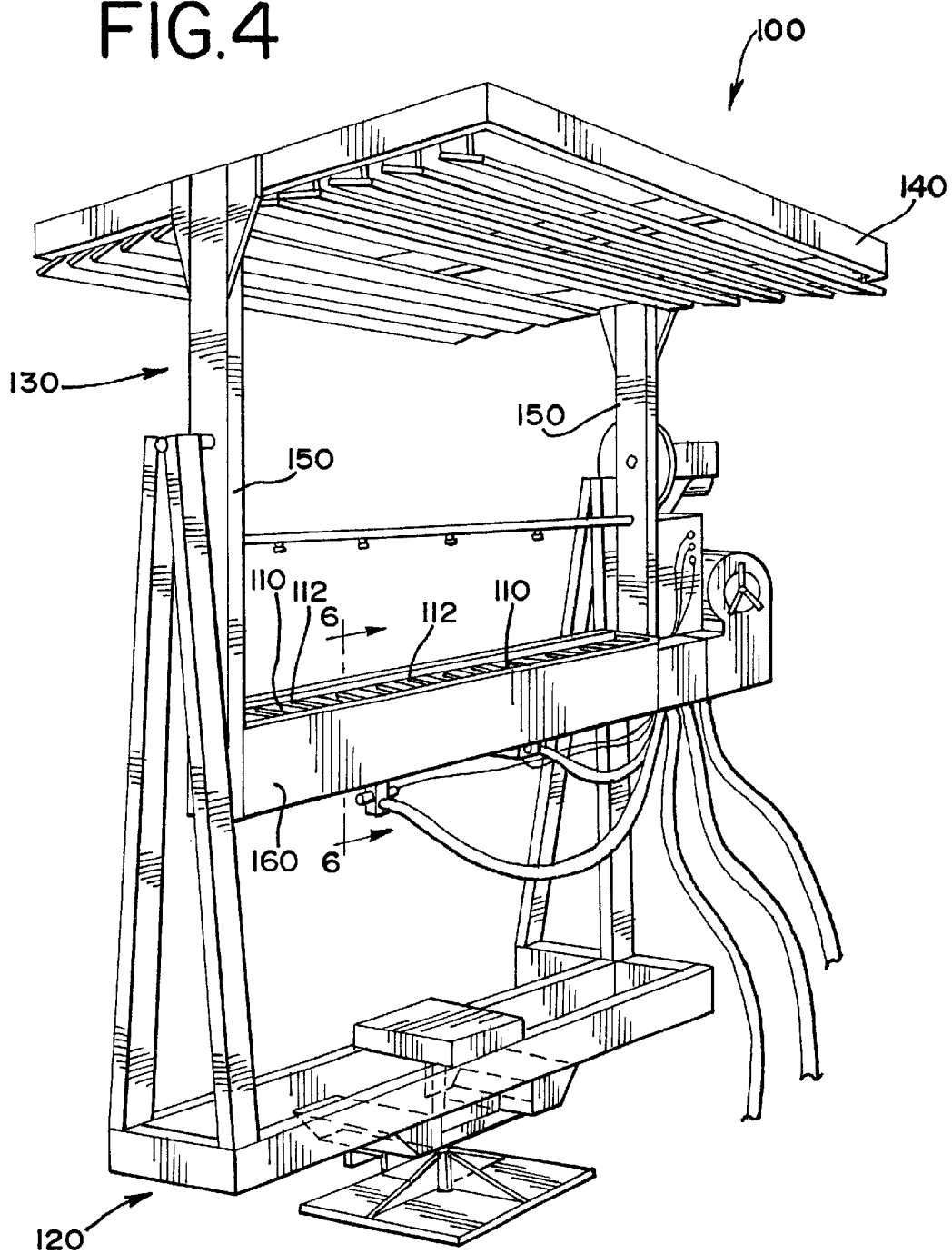
FIG. 4 is a perspective view of the accelerated weathering test apparatus of FIG. 2 in a second operative position.
Figure 5:
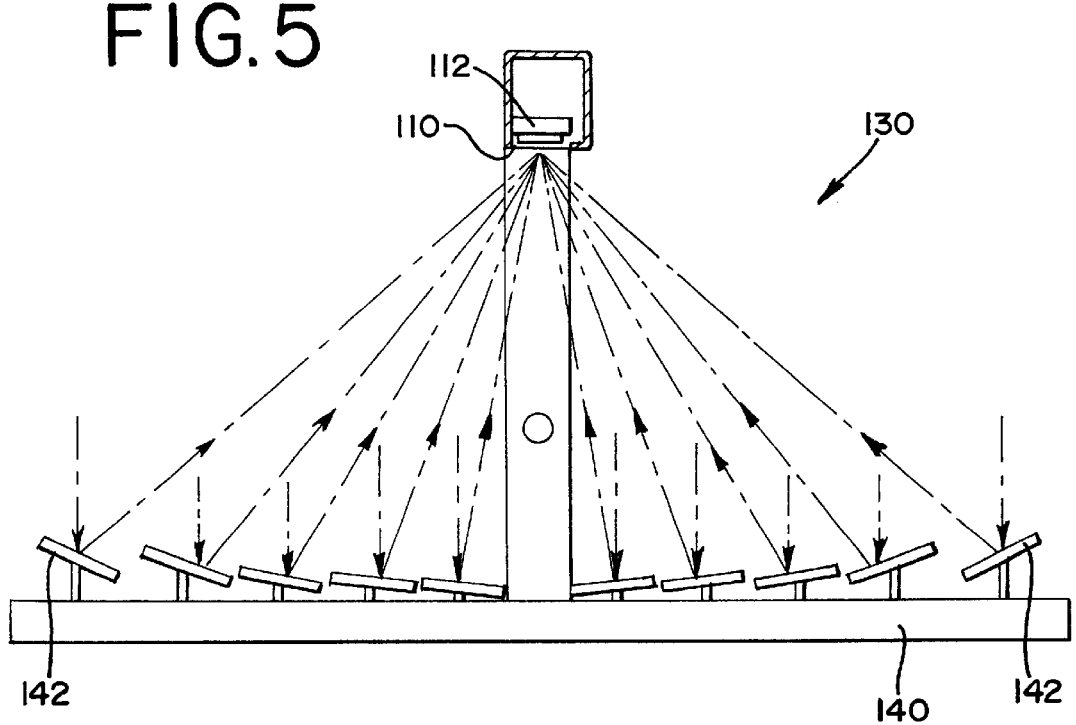
FIG. 5 is a cross-sectional view of a detail of the accelerated weathering test apparatus depicted in FIG. 2.

The support member 120 may be formed as a single-axis tracking device as shown in FIG. 1, or as a dual-axis tracking device shown in FIGS. 2–4. Both tracking devices may use any conventional solar cell tracking unit (not shown) which controls the orientation and position of the support member 120 and operative portion 130 in order to maintain the mirror bed 140 perpendicular to incident rays of sunlight. The support structure of the single-axis device shown in FIG. 1 is well-known in the art to include a pair of A-frame members 22, 24 provided with anchors 26, 28 for securing the test apparatus to the ground at its desired position. An altitude adjustment mast 30 supports A-frame member 24 at a desired adjustable height to account for periodic variation in the sun's altitude at solar noon. The apparatus axis is oriented in the north/south direction, with the north pole being altitude-adjustable to account for seasonable variations in solar altitude at zenith.

The dual-axis apparatus shown in FIGS. 2–4 provides the same function but uses different structure which is similar, namely A-frame members 122, 124 with an adjustment apparatus 126 for controlling the azimuth rotation of the accelerated weathering test apparatus 100 and the tilt elevation. Both of these support members are well-known in the art and described in ASTM Standard G 90-94. It is within the teachings of the present invention that other suitable support members could be utilized for providing adjustment of the apparatus relative to the sun.

Figure 6A:
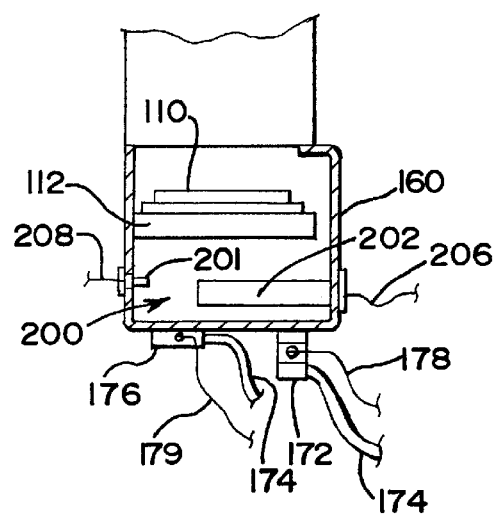
FIG. 6A is a cross-sectional view of a detail of the accelerated weathering test apparatus depicted in FIG. 4.
Figure 6B:
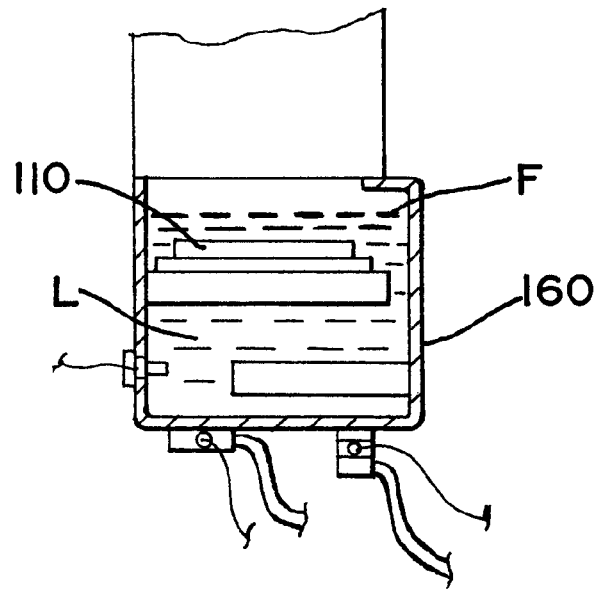
FIG. 6B is a cross-sectional view of a detail of the accelerated weathering test apparatus depicted in FIG. 4 with the specimen immersed in a liquid.
Figure 6C:
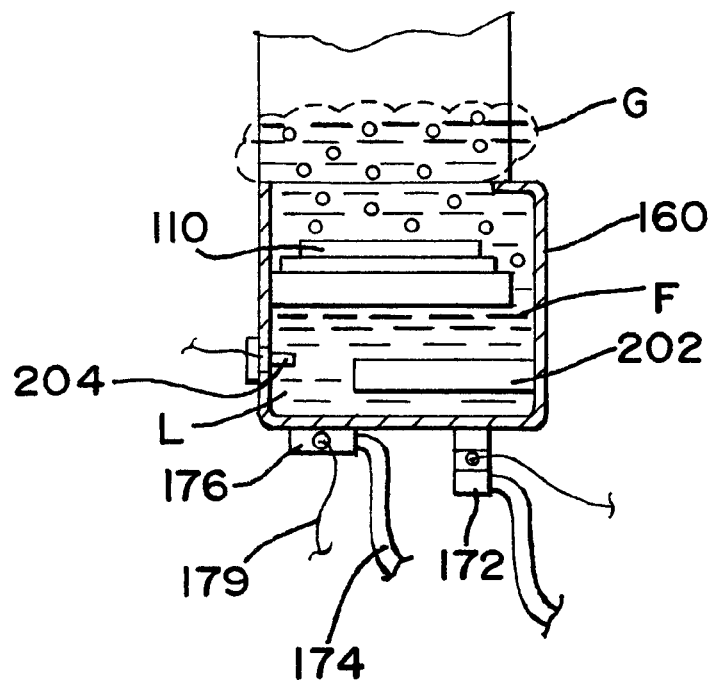
FIG. 6C is a cross-sectional view of a detail of the accelerated weathering test apparatus depicted in FIG. 4 with a liquid and a fluid solution of liquid and gas in the channel.

The standards 150 extend upwardly from and perpendicularly to the mirror bed 140. The channel 160 has a generally rectangular cross section and is supported by the upper ends of the standards 150. An air circulation mechanism 162 including a squirrel cage blower assembly 164 communicates with one end of the channel 160. The squirrel cage blower assembly 164 includes a fan driven by an electric motor to circulate cooling ambient air through the channel 160. It is within the teachings of the present invention that any conventional control system may be associated with the air circulation mechanism 162. For example, the control system may include temperature sensing panels associated with sensors to determine the temperature of the test specimens on the target board in order to selectively control the application of electrical power to the electrical motor within the squirrel cage blower assembly 163, or any other suitable control system. The channel 160 includes a deflector 164 which extends for the length of a target board and causes cooling ambient air to be circulated across the target board for cooling test samples, as also shown in FIGS. 6A–C.

A supply system 170 is operatively connected to the channel 160 for supplying a fluid to the channel 160 for immersing the at least one test specimen when the operative portion 130 is disposed in the second operative position as shown in FIG. 4. The supply system 170 includes a first valve 172 operatively connected to the channel 160 for supplying the fluid to the channel 160 and at least one fluid passageway 174 in communication with the first valve 172 for supplying the fluid. It is within the teachings of the present invention that other actuators could be utilized for the valve. For example, any suitable device which may be actuated from a closed orientation to an open orientation will perform the function of the valve. It will also be recognized that the fluid passageway 174 may be formed in any suitable manner. For example, the fluid passageway may be a flexible metal or rubber hose, a rigid conduit, a combination of hose and conduit or any other suitable passageway structure. It is further within the teachings of this invention that the fluid for immersing the test specimens may be disposed in the channel in a liquid state, a gaseous state, a solution including a combination of liquid and gas. For example, the fluid may be a water-based solution which may be heated to develop a fog or steam or any other suitable liquid, gas or liquid/gas combination.

A control device 180 is programmable to control, among other things related to the general operation of the apparatus, the first valve 172 to supply the fluid to the channel 160 such that the at least one specimen is immersed in the fluid when the operative portion 130 is disposed in the second operative position as shown in FIG. 4. The control device 180 communicates with the first valve 172 via a first signal wire 178 to activate the first valve 172 from a first operative position which is normally closed to a second operative position which is open so that the fluid may be supplied for a predetermined time through the fluid passageway 174 to the channel 160 in order to immerse the test specimens. The control device 180 also communicates with a second valve 176 via a second signal wire 179 to activate the second valve 176 which is associated with another fluid passageway 174 from a first operative position which is normally closed to a second operative position which is open such that fluid may be removed from the channel 160 via at least one fluid passageway 174. It will be recognized that the control device 180 is preferably an electrical/electronic design and that a mechanical design which can be utilized to provide identical function may also be used. For example, while a digital solid state device is preferred for simplicity, programmability, reliability and cost, it will be recognized that an analog device, such as a timer-based system will provide the same function. Further, it is also within the teachings of this invention that activation of the values can also be performed manually by an operator.

A water spray nozzle assembly 132 may be used to periodically spray water at the test specimens when the operative portion 130 is disposed in the first operative position to simulate dew, rain, etc. in a conventional, well-known manner.

An additive system 220 may include a fluid passageway 222 and a third valve 224 and is operatively connected to the supply system 170 for introducing an additive into the fluid when the operative portion 130 is disposed in the second operative position shown in FIG. 4, as will be discussed below. The control device 180 communicates with a third valve 224 via a third signal wire 226 to activate the third valve 224 from a first operative position which is normally closed to a second operative position which is open such that the additive way be introduced into the fluid in the fluid passageway 174. It will be recognized that the additive system may be configured in any suitable manner with components similar to those described above regarding valves and fluid passageways. The additives may include, but not be limited to, pollutants, corrosive agents (such as salts), solvents, solutes, organic and inorganic solids, liquids, gasses or combinations or any other suitable additive.

FIG. 3 shows a side elevation view of the accelerated weathering test apparatus 100. The mirror bed 140 supports a plurality of flat mirrors 142 which are angled relative to the end 140 to reflect solar radiation directly impinging upon such mirrors 142 to a target board (FIG. 5). The control device 180 is disposed within an enclosure 182 on the A-frame member 122 and signal wires exit through one side of the enclosure 182.

FIG. 4 shows a perspective view of the accelerated weathering test apparatus 100 disposed in the second operative position where the operative portion 130 has been moved relative to the support member 120 so that the mirror bed 140 and the channel 160 are inverted from their original positions in the first operative position as shown in FIGS. 2, 3 and 5. The standards 150 in the second operative position as shown in FIG. 4, extend downwardly and perpendicular from the mirror bed 140 to the channel 160. Test specimens 110 are supported on a target board 112 disposed in the channel 160 such that the specimens 110 are exposed to concentrated solar radiation when the operative portion 130 is disposed in the first operative position (See FIG. 5) and immersion in a fluid when the operative portion 130 is disposed in the second operative position (See FIGS. 6A–C). It will be recognized that the test specimens 110 supported the target board 112 and the target board 112 secured to the channel 160 may be each respectively secured thereto in any suitable manner. For example, the test specimens 110 or target board 112 may be secured by threaded fasteners, hook-and-loop fasteners, two-piece fasteners, adhesives or in any other suitable manner. A test cycle of the present invention is defined by oscillation of the operative portion between the first and second operative positions with the test specimen 100 supported on a target board 112 so that the test specimens 110 are exposed to solar irradiance and fluid immersion during each test cycle.

FIG. 5 shows a cross-sectional view of a detail of operative portion 130 of the accelerated weathering test apparatus disposed in the first operative position. A plurality of flat mirrors 142 are supported on and disposed at various angles relative to the mirror bed 140 such that the solar radiation, indicated by the dashed lines, is concentrated on the test specimens 110 mounted on the target board 112. Conventional, well-known tracking devices including sensors and actuators track the movement of the sun relative to the accelerated weathering test apparatus and reposition the accelerated weathering test apparatus as discussed above so that a desired amount of solar radiation is concentrated on a test specimens 110. It will be recognized that operation of the accelerated weathering test apparatus disposed in the first operative position may be in accordance with any suitable manner.

FIG. 6A shows a cross-sectional view of a detail of the channel 160 of the operative portion disposed in the second operative position. The target board 112 disposed within the channel 160 supports the test specimens 110. The first valve 172 is connected to the channel 160 to provide communication between the channel 160 and the fluid passageway 174 for introducing fluid into the channel 160. A signal wire 178 connects the control device to the first valve 172 so that the control device may activate the first valve 172 in any suitable manner discussed above. The second valve 176 is connected to the channel 160 to provide communication between the channel fluid passageway 174 for removing the fluid from the channel 160 through the fluid passageway 174. A signal wire 179 connects the control device to the second valve 176 so that the control device may activate the second valve 176 from a first operative position which is normally closed to a second operative position which is open so that fluid may be removed from the channel 160. It is within the teachings of the present invention that other configurations could be utilized to remove the fluid from the channel 160. For example, the fluid may be removed from the channel 160 by drain apertures formed in the channel, by moving the operative portion to the first operative position or in any other suitable manner.

A temperature control system 200 including a temperature adjusting element 202 and a temperature sensor 204 may be disposed in the channel 160 for controlling a temperature of the fluid. Signal wires 206, 208 respectively connect the temperature adjusting element 202 and the temperature sensor 204 to the control device which may be programmed with a temperature set point or a series of temperature set points. It will be recognized that the temperature adjusting element 202 and the temperature sensor 204 may be configured in any suitable manner which is compatible with the control device. For example, the temperature adjusting element may be configured as a resistive heating element or have any other suitable configuration and the temperature sensor may be configured as a thermocouple or have any other suitable configuration. Further, it will be recognized that the temperature control system may be controlled automatically or manually for a set point, a series of set points, operational and manner of operation. As shown in FIG. 6A, the operative portion has been moved to the second operative position. However, the first valve 172 has not yet been activated by the control device and remains in its first operative position which is normally closed. Accordingly, no fluid can enter the channel 160 via fluid passageway 174.

FIG. 6B shows a cross-sectional view of a detail of the channel 160 of the operative portion where the first valve 174 was opened for a predetermined period of time so that the specimen 110 is immersed in a liquid L. The fill line F indicates the level to which the liquid L fills the channel 160 in this embodiment. The test specimens 110 are disposed below the fill line F. The fluid in this embodiment is in a liquid state. It will be recognized that it is within the teachings of the present invention that the fluid may be in a gaseous state or a combination of liquid and gas. In particular, FIG. 6C shows a cross-sectional view of a detail of the channel 160 of the operative portion wherein the liquid L is disposed in the channel 160 at a fill line F such that the test specimens 110 are disposed above the fill line F. It will be recognized that the control device deactivated the first valve 172 after expiration of a predetermined period of time which is less than the period discussed above. Accordingly, the fill line F is lower. The control device is operatively connected to the temperature adjusting element 202 and temperature sensor 204 to control the temperature of the liquid L in this embodiment such that the fluid immerses the test specimens 110 in a gas G. Generally, the gas G is formed by heating the fluid to a predetermined temperature such that the gas G develops from the liquid L. However, it is within the teachings of the present invention that other methods of developing a gas from a liquid may be performed such as evaporation, diffusion, volitization, etc. For example, it may be necessary to cool a liquid to develop a gas, or any other suitable manner.

The control device is operatively connected to the second valve 176 by the signal wire 179 so that the control device may activate the second valve 176 from a first operative position which is normally closed to a second position which is open so that the liquid L disposed within the channel 160 (See FIGS. 6B and 6C) may be removed from the channel 160 via fluid passageway 174. After a predetermined period of time, the fluid in FIGS. 6B and 6C will be removed in this manner.

In operation, the control device is programmable for controlling the accelerated weathering test apparatus to function to: (1) oscillate the operative portion between the first and second operative positions for predetermined periods of time to define a test cycle; (2) track the sun when the operative portion is disposed in the first operative position for concentrating solar irradiance in the test specimens; (3) operate the air circulation mechanism; (4) oscillate the first valve between a first operative position and a second operative position for predetermined periods of time, such that the fluid flows through the fluid passageways and the first valve to fill the channel to a desired fill line and the at least one test specimen is immersed in the fluid for a predetermined period of time; (5) control a temperature control system such that a temperature of the fluid is maintained at a desired temperature set point for a predetermined period of time; and (6) oscillate a second valve from a first operative position and a second operative position for predetermined periods of time such that the fluid flows through the second valve emptying the channel.

In operation, the accelerated weathering test apparatus is used for accelerated weathering testing. The accelerated weathering test apparatus includes at least one support member, an operative portion operatively connected to at least one support member including a mirror bed, at least one standard, at least one channel, a channel having a target board disposed therein, an air circulation mechanism in communication with the channel, a supply system including a first valve operatively connected to the channel for supplying a fluid to the channel and a control device for controlling the accelerated weathering test apparatus and the first valve. First, at least one test specimen is mounted on the target board. Second, the control device is programmed to function to execute a test cycle including the steps of: (1) activating the air circulation mechanism; (2) activating a solar tracking system for a first predetermined period of time; (3) deactivating a solar tracking system upon expiration of the first predetermined period of time; (4) rotating the operative portion from the first operative position to the second operative position; (5) deactivating the air circulation mechanism; (6) activating a first valve for a second predetermined period of time from a first operative position normally closed to a second operative position open such that the fluid is supplied through the fluid passageways and the first valve and into the channel; (7) deactivating the first valve from the first operative position to the second position upon expiration of the second predetermined period of time such that the fluid in the channel is at a desired fill line; (8) exposing the at least one test specimen for a third predetermined period of time; (9) removing the fluid from the channel; and (10) repeating steps (1) through (9) for a desired number of testing cycles.

In another embodiment, the accelerated weathering test apparatus may further include a temperature control system including a temperature adjusting element and a temperature sensor disposed in the channel for controlling a temperature of the fluid. The testing cycle may then be modified in this embodiment to further include the steps of: (1) activating the temperature adjusting element during the third predetermined period of time for a fourth predetermined period of time; (2) monitoring the temperature of the fluid with the temperature sensor; (3) maintaining the temperature of the fluid at a set point or a series of set points; and (4) deactivating the temperature adjusting element upon expiration of the fourth predetermined period of time.

In another embodiment, the supply system further includes an additive system for introducing an additive into the fluid. The testing cycle may then be modified in this embodiment to further include the steps of: (1) activating the additive system during the second predetermined period of time for a fifth predetermined period of time; (2) introducing an additive into the fluid being supplied to the channel; and (3) deactivating the additive system upon expiration of the fifth predetermined period of time.

In another embodiment, the supply system may further include a second valve for removing the fluid from the channel. The testing cycle may be modified in this embodiment to further include the steps of: (1) activating the second value from a first operative position normally closed to a second operative position open for a sixth predetermined period of time upon expiration of the third predetermined period of time; and (2) deactivating the second valve from the second operative position to the first operative position upon expiration of the sixth predetermined period of time such that the fluid is removed from the channel.

It is to be understood that while the invention has been described in conjunction with the detailed description thereof, the foregoing description is intended to illustrate and not to limit the scope of the invention. For example, any of the operations, activations or actuations described related to this invention may be accomplished by manual manipulation by an operator within the teachings of this invention. Other implementations are within the scope of the following claims.

What is claimed is:

1. An accelerated weathering test apparatus for concentrating solar irradiance upon and immersing at least one test specimen, comprising:

at least one support member;

an operative portion operatively connected to the at least one support member including a mirror bed, at least one standard and a channel;

the operative portion moveable relative to the at least one support member from a first operative position to a second operative position; and, a target board disposed in the channel for supporting the at least one test specimen for exposure to concentrated solar radiation when the operative portion is disposed in the first operative position and immersion in a fluid located within the channel when the operative portion is disposed in the second operative position.

2. The apparatus as recited in claim 1, wherein the fluid is in a liquid state.

3. The apparatus as recited in claim 1, wherein a temperature control system including a temperature adjusting element and a temperature sensing element is disposed in the channel for controlling a temperature of the fluid.

4. The apparatus as recited in claim 1, wherein the operative portion oscillates between the first and second operative positions with the at least one test specimen supported on the target board, to define a test cycle wherein the test specimen is exposed to solar irradiance and fluid immersion during each test cycle.

5. The apparatus as recited in claim 1, wherein a supply system is operatively connected to the channel for supplying the fluid to the channel for immersing the at least one test specimen when the operative portion is disposed in the second operative position.

6. The apparatus as recited in claim 5, wherein an additive system is operatively connected to the supply system for introducing an additive into the fluid when the operative portion is in the second operative position.

7. An accelerated weathering test apparatus for concentrating solar irradiance upon and immersing at least one test specimen including at least one support member and an operative portion operatively connected to the at least one support member including a mirror bed, at least one standard, a channel and an air circulation mechanism in communication with the channel, where the operative portion is moveable relative to the at least one support member from a first operative position to a second operative position, the apparatus comprising:

a target board disposed in the channel for mounting the at least one test specimen for exposure to concentrated solar irradiance when the operative portion is disposed in the first operative position and immersion in a fluid when the operative portion is disposed in the second operative position;

a supply system including a first valve and at least one fluid passageway operatively connected to the channel for supplying the fluid to the channel; and a control device for controlling the first valve to supply the fluid to the channel such that the at least one test specimen is immersed in the fluid when the operative portion is in the second operative position.

8. The apparatus as recited in claim 7, wherein the at least one test specimen is securely mounted to the target board with threaded fasteners.

9. The apparatus as recited in claim 7, wherein the control device activates the first valve from a first operative position normally closed to a second operative position open so that fluid is supplied for a pre-determined time through the at least one fluid passageway to the channel to immerse the at least one test specimen.

10. The apparatus as recited in claim 7, wherein the control device controls a second valve and activates the second valve from a first operative position normally closed to a second operative position open such that fluid is removed from the channel.

11. The apparatus as recited in claim 7, wherein a temperature control system including a temperature control element and a temperature sensing element is disposed in the channel for controlling a temperature of the fluid.

12. The apparatus as recited in claim 11, wherein the control device is operatively connected with the temperature adjusting element and a temperature sensing element for controlling the temperature of the fluid to at least one temperature set point.

13. The apparatus as recited in claim 7, wherein the control device is programmable for controlling the accelerated weathering test apparatus to function to: (1) oscillate the operative portion between the first and second operative positions for pre-determined periods of time to define a test cycle; (2) track the sun when the operative portion is disposed in the first operative position for concentrating solar irradiance on the at least one test specimen; (3) operate the air circulation mechanism; (4) oscillate the first valve between a first operative position and a second operative position for pre-determined periods of time; (5) such that the fluid flows through the at least one fluid passageway and the first valve to fill the channel to a desired fill line and the at least one test specimen is immersed in the fluid for a predetermined period of time; (6) control a temperature control system such that a temperature of the fluid is maintained at at least one temperature set point for a predetermined period of time with respect to each at least one temperature set point ; and (7) oscillate a second valve between a first operative position and a second operative position for predetermined periods of time such that the fluid flows through the second valve emptying the channel.

14. A method for accelerated weathering testing comprising:

(a) providing an accelerated weathering test apparatus including at least one support member, an operative portion operatively connected to the at least one support member including a mirror bed, at least one standard, a channel having a target board disposed therein, an air circulation mechanism in communication with the channel, a supply system including a first valve operatively connected to the channel for supplying a fluid to the channel and a control device for controlling the accelerated weathering test apparatus and the first valve;

(b) mounting at least one test specimen on the target board;

(c) programming the control device to function to execute a test cycle including the steps of:

(0) rotating the operative portion to a first operative position for exposing the at least one test specimen to a concentrated solar irradiance;

(1) activating the air circulation mechanism;

(2) activating a solar tracking system for a first predetermined period of time;

(3) deactivating the solar tracking system upon expiration of the first predetermined period of time;

(4) rotating the operative portion from the first operative position to a second operative position for exposing the at least one test specimen to immersion in a fluid in the channel;

(5) deactivating the air circulation mechanism;

(6) activating a first valve for a second predetermined period of time from a first operative position normally closed to a second operative position open such that the fluid is supplied through the fluid passageways and the first valve and into the channel;

(7) deactivating the first valve from the first operative position to the second operative position upon expiration of the second predetermined period of time such that the fluid in the channel is at a desired fill line;

(8) exposing the at least one test specimen to immersion in the third for a third predetermined period of time;

(9) removing the fluid from the channel; and

(10) repeating steps (0) through (10) for a desired number of testing cycles.

15. The method as recited in claim 14, wherein the accelerated weathering test apparatus further includes a temperature control system including a temperature adjusting element and a temperature sensor disposed in the channel for controlling a temperature of the fluid.

16. The method as recited in claim 15, wherein the testing cycle further includes the steps of:

(a) activating the temperature adjusting element during the third predetermined period of time for a fourth predetermined period of time;

(b) monitoring the temperature of the fluid with the temperature sensor;

(c) maintaining the temperature of the fluid at at least one temperature set-point;

(d) deactivating the temperature adjusting element upon expiration of the fourth predetermined period of time; and (e) Repeating steps (a) through (d) for each at least one temperature set point.

17. The method as recited in claim 14, wherein the supply system further includes an additive system for introducing an additive into the fluid.

18. The method as recited in claim 17, wherein the testing cycle further includes the steps of:

(a) activating the additive system during the second predetermined period of time for a fifth predetermined period of time;

(b) introducing an additive into the fluid being supplied to the channel; and (c) deactivating the additive system upon expiration of the fifth predetermined period of time.

19. The method as recited in claim 14, wherein the supply system further includes a second valve for removing the fluid from the channel.

20. The method as recited in claim 19, wherein the testing cycle further includes the steps of:

(a) activating the second valve from a first operative position normally closed to a second operative position open for a sixth predetermined period of time upon expiration of the third predetermined period of time; and (b) deactivating the second valve from the second operative position to the first operative position upon expiration of the sixth predetermined period of time.

* * * * *